United States Patent [19]

Suzuki et al.

[11] Patent Number: 5,066,825

[45] Date of Patent: Nov. 19, 1991

[54] PROCESS FOR PREPARING A NAPHTHALENE DERIVATIVE

[75] Inventors: Takashi Suzuki, Kawanishi; Minehiko Yamamura, Itami; Shinichi Yamada, Ashiya, all of Japan

[73] Assignee: Tanabe Seiyaku Co., Ltd., Osaka, Japan

[21] Appl. No.: 437,065

[22] Filed: Nov. 16, 1989

[30] Foreign Application Priority Data

Nov. 29, 1988 [JP] Japan .................................. 303335

[51] Int. Cl.$^5$ ............................................ C07C 69/76
[52] U.S. Cl. ............................................... 560/56
[58] Field of Search ........................................ 560/56

[56] References Cited

U.S. PATENT DOCUMENTS 4,771,072 9/1988 Iwasaki ............................. 514/533

FOREIGN PATENT DOCUMENTS 0188248 7/1986 European Pat. Off. .

OTHER PUBLICATIONS

Plaumann et al., "Potential Isobenzofurans: Their Use in the Synthesis of Naturally Occurring 1-Arylnaphthalide Lignans", The Journal of the Chemical Society, Chemical Communications, 1980, pp. 354, 355, Royal Society of Chemistry, London, GB H.P.

*Primary Examiner*—Paul J. Killos
*Attorney, Agent, or Firm*—Browdy and Neimark

[57] ABSTRACT

A novel process for preparing a naphthalene derivative of the formula:

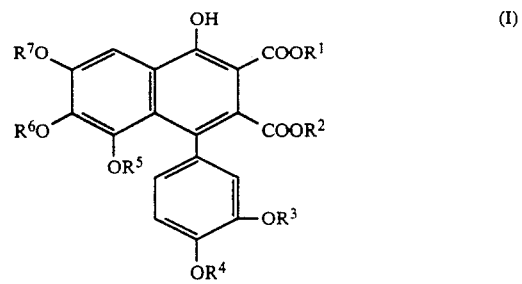

wherein $R^1$, $R^2$, $R^3$, $R^4$, $R^5$, $R^6$ and $R^7$ are a lower alkyl group, and an intermediate thereof is disclosed. Said naphthalene derivative (I) and a pharmaceutically acceptable salt thereof are useful as a hypolipidemic agent.

10 Claims, No Drawings

PROCESS FOR PREPARING A NAPHTHALENE DERIVATIVE

This invention relates to a process for preparing a naphthalene derivative. More particularly, it relates to a novel process for preparing a naphthalene derivative of the formula:

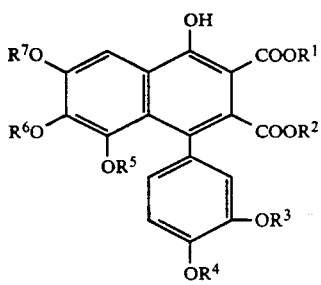

wherein $R^1$, $R^2$, $R^3$, $R^4$, $R^5$, $R^6$ and $R^7$ are a lower alkyl group.

The naphthalene derivative (I) and pharmaceutically acceptable salts thereof are useful as a hypolipidemic agent.

It is hitherto known that the above-mentioned naphthalene derivative(I) can be prepared by reacting a 3,4-di(lower alkoxy)benzaldehyde with a 2-bromo-3,4,5-tri(lower alkoxy)benzaldehyde di-lower alkyl acetal and reacting the product with a di-lower alkyl acetylenedicarboxylate (U.S. Pat. No.4,771,072).

However, the known method is still disadvantageous for preparing the naphthalene derivative (I) on an industrial scale in that, since the 2-bromo-3,4,5-tri(lower alkoxy)benzaldehyde di-lower alkyl acetal to be used as the starting compound has to be prepared by brominating a 3,4,5-tri(lower alkoxy)benzaldehyde before acetalization thereof, it is impossible to avoid the use of bromine which is harmful and difficult to handle.

An object of the present invention is to provide a novel method by which the naphthalene derivatives (I) can be prepared without using bromine. Another object of the present invention is to provide a novel method by which the naphthalene derivative (I) can be prepared from the 3,4,5-tri(lower alkoxy)benzaldehyde di-lower alkyl acetal in only two steps. Other object of the present invention is to provide an industrially advantageous method for preparing an intermediate of the naphthalene derivative (I).

As a result of the various investigations, the inventors of the present invention have now found that an addition reaction occurs between a non-brominated 3,4,5-tri(lower alkoxy)benzaldehyde di-lower alkyl acetal and a 3,4-di(lower alkoxy)benzaldehyde to give a 2-(3,4-di lower alkoxy)-α-hydroxybenzyl)-3,4,5-tri(lower alkoxy)benzaldehyde di-lower alkyl acetal in a high yield.

According to the present invention, the naphthalene derivative (I) or a pharmaceutically acceptable salt thereof can be prepared by the steps of:

A) reacting a di(lower alkoxy)benzaldehyde of the formula:

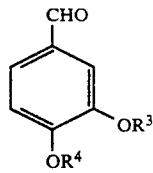

wherein $R^3$ and $R^4$ are the same as defined above, with a tri(lower alkoxy)benzaldehyde di-lower alkyl acetal of the formula:

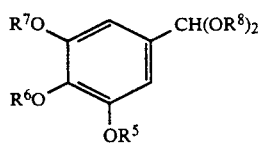

wherein $R^5$, $R^6$ and $R^7$ are the same as defined above and $R^8$ is a lower alkyl group, to give an α-hydroxybenzylbenzaldehyde compound of the formula:

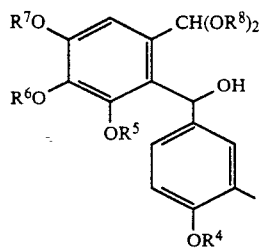

wherein $R^3$, $R^4$, $R^5$, $R^6$, $R^7$ and $R^8$ are same as above,

B) reacting the compound (IV) or a salt thereof with an acetylenedicarboxylate of the formula:

$$R^1OOC-C\equiv C-COOR^2 \quad (V)$$

wherein $R^1$ and $R^2$ are the same as defined above, and

C) if required, further converting the product into a pharmaceutically acceptable salt thereof.

In the above-mentioned reactions, examples of the lower alkyl group shown by symbols $R^1$, $R^2$, $R^3$, $R^4$, $R^5$, $R^6$, $R^7$ and $R^8$ include straight or branched alkyl group of one to four carbon atoms such as methyl, ethyl, n-propyl, isopropyl or butyl.

The reaction of di(lower alkoxy)benzaldehyde (II) and the tri(lower alkoxy)benzaldehyde di-lower alkyl acetal (III) can be conducted in the presence of an organic lithium compound in a solvent. Examples of the organic lithium compound include lower alkyl lithiums such as n-butyl lithium, aryl lithiums such as phenyl lithium and lithium di-lower alkyl amides such as lithium diisopropyl amide. Preferred amount of the organic lithium compound to be used in the above reaction is 1 to 3 moles, especially 1 to 2 moles, per mole of the compound (III). Hexane, tetrahydrofuran, ether, dioxane, benzene, toluene, xylene and the like may be used as the solvent. It is preferred to carry out the reaction at a temperature of −70° to 40° C., especially −20° to 20° C.

The reaction of the α-hydroxybenzylbenzaldehyde di-lower alkyl acetal compound (IV) and the acetylenedicarboxylate (V) can be carried out in the presence of an acid either in a solvent or without solvent. Examples of the acid include mineral acids such as hydrochloric acid or sulfuric acid and organic acids such as formic acid, acetic acid, trifluoroacetic acid, p-toluenesulfonic acid or methanesulfonic acid. In case that the reaction is carried out in a solvent, the same solvents as used in the reaction of the compound (II) and compound (III) may be preferably used as the solvent. It is preferred to carry out the reaction at a temperature of 0° to 150° C., especially 50° to 100° C.

The thus-obtained naphthalene derivative (I) can be readily converted into a pharmaceutically acceptable salt thereof by treating said compound with a base such as alkali metal hydroxides (e.g., sodium hydroxide), alkaline earth metal hydroxides (e.g., lithium hydroxide) or quaternary ammonium hydroxide.

As mentioned hereinbefore, in comparison with the known method disclosed in U.S. Pat. No.4,771,072, the method of the present invention is quite more advantageous in that the naphthalene derivative (I) can be prepared without using harmful bromine, and that said derivative (I) can be prepared in one less steps.

EXAMPLE 1

(1) A mixture of 196.2 g of 3,4,5-trimethoxybenzaldehyde, 127.3 g of trimethoxymethane, 200 ml of methanol and 0.1 g of hydrochloric acid is refluxed for 3 hours. After cooling the reaction mixture, 0.2 g of a 24% sodium methoxide solution in methanol is added thereto and the mixture is evaporated under reduced pressure to remove solvent. 150 ml of tetrahydrofuran are added to the residue, and the mixture is evaporated under reduced pressure to remove solvent. 243 g of 3,4,5-trimethoxybenzaldehyde dimethyl acetal are thereby obtained as a pale yellow oil.

IR$\nu_{max}^{Neat}$(cm$^{-1}$): 1600, 1500, 1460, 1420, 1360, 1230, 840

(2-a) 136 ml of a 1.6M n-butyl lithium solution in hexane are added to a solution of 48.5 g of 3,4,5-trimethoxybenzaldehyde dimethyl acetal in 485 ml of tetrahydrofuran under stirring at 0° C. for about 20 minutes. The mixture is further stirred at 0° C. for 30 minutes, and 33.2 g of 3,4-dimethoxybenzaldehyde are added thereto. After stirring the mixture at 0° to 10° C. for 2 hours, 780 ml of water and 780 ml of ethyl acetate are added thereto. After shaking the mixture, the organic layer is separated therefrom, washed with water and evaporated under reduced pressure to remove solvent. 81.0 g of 2-(3,4-dimethoxy-α-hydroxybenzyl)-3,4,5-trimethoxybenzaldehyde dimethyl acetal are thereby obtained as a yellow oil.

IR$\nu_{max}^{Nujol}$(cm$^{-1}$): ) 3500, 2930, 1600

(2-b) 136 ml of a 1.6M n-butyl lithium solution in hexane are added to a solution of 48.5 g of 3,4,5-trimethoxybenzaldehyde dimethyl acetal in 485 ml of benzene under stirring at 0° C. for about 20 minutes. The mixture is further stirred at 0° C. for 30 minutes, and 33.2 g of 3,4-dimethoxybenzaldehyde are added thereto. After stirring the mixture at 0° to 10° C. for 2 hours, 485 ml of water and 16 g of citric acid are added thereto. After shaking the mixture, the organic layer is separated therefrom, washed with water and evaporated under reduced pressure to remove solvent. 78.5 g of 2-(3,4-dimethoxy-α-hydroxybenzyl)-3,4,5-trimethoxybenzaldehyde dimethyl acetal are thereby obtained as a yellow oil.

The physico-chemical properties of this product are identical with those of the product obtained in Paragraph (2-a).

(2-c) 136 ml of a 1.6M n-butyl lithium solution in toluene are added to a solution of 48.5 g of 3,4,5-trimethoxybenzaldehyde dimethyl acetal in 485 ml of tetrahydrofuran under stirring at 0° C. for about 20 minutes. The mixture is further stirred at 0° C. for 30 minutes, and 33.2 g of 3,4-dimethoxybenzaldehyde are added thereto. After stirring the mixture at 0° to 10° C. for 2 hours, 780 ml of water and 780 ml of ethyl acetate are added thereto. After shaking the mixture, the organic layer is separated therefrom, washed with water and evaporated under reduced pressure to remove solvent. 79.5 g of 2-(3,4-dimethoxy-α-hydroxybenzyl)-3,4,5-trimethoxybenzaldehyde dimethyl acetal are thereby obtained as a yellow oil.

The physico-chemical properties of this product are identical with those of the product obtained in Paragraph (2-a).

(3) 49.5 g of 2-(3,4-dimethoxy-α-hydroxybenzyl)-3,4,5-trimethoxybenzaldehyde dimethyl acetal are dissolved in 5 ml of toluene. 14.2 g of dimethyl acetylenedicarboxylate and 19 mg of p-toluenesulfonic acid monohydrate are added to the solution, and the mixture is refluxed for 3 hours. After cooling the reaction mixture, 200 ml of methanol are added thereto, and the mixture is allowed to stand at −30° C. overnight. The precipitated crystals are collected by filtration and recrystallized from ethyl acetate to give 33.1 g of 1-(3,4-dimethoxyphenyl)-2,3-bis(methoxycarbonyl)-4-hydroxy-6,7,8-trimethoxynaphthalene as colorless prisms.

M. p. 182°–183° C.

IR$\nu_{max}^{Nujol}$(cm$^{-1}$): 2950, 1740, 1660, 1510, 810

(4) A solution of 4.86 g of 1-(3,4-dimethoxyphenyl)-2,3-bis(methoxycarbonyl)-4-hydroxy-6,7,8-trimethoxynaphthalene in 100 ml of tetrahydrofuran is added to a suspension of 0.387 g of 62.5% sodium hydride in 10 ml of tetrahydrofuran under stirring at room temperature, and the mixture is stirred at the same temperature for 1 hour. Then, the mixture is evaporated at a temperature below 30° C. under reduced pressure to remove solvent, and the residue is triturated by petroleum ether to give 4.8 g of 1-(3,4-dimethoxyphenyl)-2,3-bis(methoxycarbonyl)-4-hydroxy-6,7,8-trimethoxynaphthalene sodium salt as powder.

IR$\nu_{max}^{KBr}$(cm$^{-1}$): 1710 (s), 1680, 1600

EXAMPLE 2

40.8 g of 2-(3,4-dimethoxy-α-hydroxybenzyl)-3,4,5-trimethoxybenzaldehyde dimethyl acetal and 17.0 g of diethyl acetylenedicarboxylate are treated in the same manner as described in Example 1-(3) to give 1-(3,4-dimethoxyphenyl)-2,3-bis(ethoxycarbonyl)-4-hydroxy-6,7,8-trimethoxynaphthalene. Yield: 43%

M. p. 138°–140° C.

EXAMPLE 3 TO 6

(1) The corresponding starting compounds are treated in the same manner as described in Example 1-(1) and (2) to give the following compounds as shown in Table 1.

TABLE 1

| Ex. Nos. | $R^3$ | $R^4$ | Physico-chemical properties etc. |
|---|---|---|---|
| 3-(1) | $CH_3$ | $C_2H_5$ | yield: 72% oil NMR(DMSO-$d_6$)δ:1.26(t, 3H), 2.89(s, 3H), 3.26(s, 3H), 3.61 (s, 3H), 3.68(s, 3H), 3.74(s, 3H), 3.78(s, 3H), 3.93(q, 2H), 5.49(s, 1H), 3.58(d, 1H, J=5Hz), 6.11(d, 1H), 6.5-7.0(m, 4H) |
| 4-(1)* | $C_2H_5$ | $CH_3$ | yield: 70% oil |
| 5-(1) | $C_2H_5$ | $C_2H_5$ | Yield: 63% oil NMR(DMSO-$d_6$)δ:1.27(t, 6H), 2.86 (s, 3H), 3.27(s, 3H), 3.60(s, 3H) 3.74(s, 3H), 3.76(s, 3H), 3.89(q, 2H), 3.94(q, 2H), 5.48(s, 1H), 3.58(d, 1H, J=5Hz), 6.10(d, 1H), 6.5-7.0(m, 4H) |
| 6-(1)* | $(CH_2)_2CH_3$ | $(CH_2)_2CH_3$ | yield: 65% oil |

*The products obtained in Examples 4-(1) and 6-(1) were used for the subsequent reaction without measuring physico-chemical properties thereof.

(2) The compounds obtained in Paragraph (1) and dimethyl acetylenedicarboxylate are treated in the same manner as described in Example 1-(3) to give the following compounds as shown in Table 2.

TABLE 2

| Ex. Nos. | $R^3$ | $R^4$ | Physico-chemical properties |
|---|---|---|---|
| 3-(2) | $CH_3$ | $C_2H_5$ | Yield: 64% colorless needles M.P. 159° C. |
| 4-(2) | $C_2H_5$ | $CH_3$ | yield: 62% colorless needles M.p. 158° C. |
| 5-(2) | $C_2H_5$ | $C_2H_5$ | Yield: 60% colorless crystals M.p. 138-140° C. |
| 6-(2) | $(CH_2)_2CH_3$ | $(CH_2)_2CH_3$ | yield: 55% colorless needles M.p. 132° C. |

What we claim is:

1. In a process for preparing a naphthalene derivative of the formula:

wherein $R^1$, $R^2$, $R^3$, $R^4$, $R^5$, $R^6$ and $R^7$ are a lower alkyl group, or a pharmaceutically acceptable salt thereof, which comprises the steps of:

A) reacting a compound of the formula:

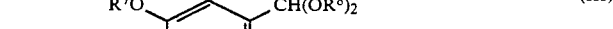

wherein $R^3$ and $R^4$ are the same as defined above, with a compound of the formula:

wherein $R^5$, $R^6$ and $R^7$ are the same as defined above and $R^8$ is a lower alkyl group, to give a compound of the formula;

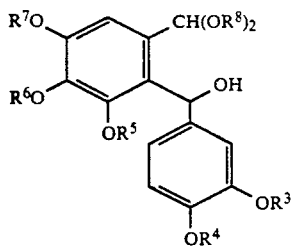

wherein $R^3$, $R^4$, $R^5$, $R^6$, $R^7$ and $R^8$ are the same as defined above, B) reacting the compound (IV) or a salt thereof with a compound of the formula:

    (V)

wherein $R^1$ and $R^2$ are the same as defined above, and

C) if required, further converting the product into a pharmaceutically acceptable salt thereof; the improvement comprising using a non-brominated compound for compound (III).

2. The process according to claim 1, wherein the reaction of the compound (II) with the compound (III) is carried out in the presence of an organic lithium compound.

3. The process according to claim 2, wherein the organic lithium compound is a lower alkyl lithium, an aryl lithium or a lithium di-lower alkyl amide.

4. The process according to claim 2, wherein the organic lithium compound is n-butyl lithium.

5. The process according to claim 2, wherein $R^1$ and $R^2$ are methyl or ethyl, $R^3$ and $R^4$ are methyl, ethyl or isopropyl, and $R^5$, $R^6$, $R^7$ and are methyl.

6. In a process for preparing a compound of the formula:

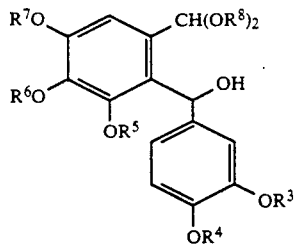

wherein $R^3$, $R^4$, $R^5$, $R^6$, $R^7$ and $R^8$ are a lower alkyl group which comprises the step of reacting a compound of the formula:

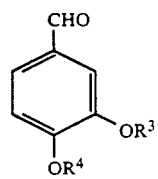

wherein $R^3$ and $R^4$ are the same as defined above, with a compound of the formula:

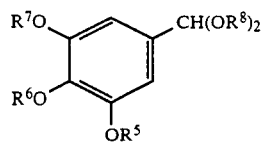

wherein $R^5$, $R^6$, $R^7$ and $R^8$ are the same as defined above; the improvement comprising using a non-brominated compound for compound III.

7. The process according to claim 6, wherein the reaction of the compound (II) with the compound (III) is carried out in the presence of an organic lithium compound.

8. The process according to claim 7, wherein the organic lithium compound is a lower alkyl lithium, an aryl lithium or a lithium di-lower alkyl amide.

9. The process according to claim 7, wherein the organic lithium compound is n-butyl lithium.

10. The process according to claim 7, wherein $R^3$ and $R^4$ are methyl, ethyl or isopropyl, and $R^5$, $R^6$, $R^7$ and $R^8$ are methyl.

* * * * *